United States Patent [19]

Long et al.

[11] 4,343,767
[45] Aug. 10, 1982

[54] CHROMATOGRAPHY APPARATUS WITH ELECTROCHEMICAL DETECTOR HAVING CARBON-BLACK CONTAINING WORKING ELECTRODE

[75] Inventors: Merton W. Long; James D. McLean; David N. Armentrout; Harold H. Gill, all of Midland, Mich.

[73] Assignee: The Dow Chemical Company, Midland, Mich.

[21] Appl. No.: 252,665

[22] Filed: Apr. 9, 1981

Related U.S. Application Data

[63] Continuation of Ser. No. 870,554, Jan. 18, 1978, abandoned.

[51] Int. Cl.$^3$ ............................................. G01N 31/08
[52] U.S. Cl. .................................. 422/70; 73/61.1 C; 204/1 T; 204/195 R; 204/294
[58] Field of Search ................... 204/195 R, 294, 1 K; 429/42, 217; 422/70; 73/61.1 C

[56] References Cited

U.S. PATENT DOCUMENTS

| | | | |
|---|---|---|---|
| 2,664,453 | 12/1953 | Lang | 429/217 |
| 2,876,189 | 3/1959 | Spracklen et al. | 204/195 R |
| 3,164,796 | 1/1965 | Dixon | 252/510 |
| 3,258,415 | 6/1966 | Kordesch | 204/195 R |
| 3,367,849 | 2/1968 | Blaedel et al. | 204/1 T |
| 3,507,773 | 4/1970 | Grangaard | 204/294 |
| 3,556,856 | 1/1971 | Elbert | 429/42 |
| 3,676,222 | 7/1972 | Deibert | 429/42 |

OTHER PUBLICATIONS

Gaylor, V. F. et al., Anal. Chem., vol. 29, pp. 224–228, Feb. 1957.
Pungor, E. et al., Magyar Kemiai Folyoirat, vol. 77, pp. 289–298, (1971).
Pungor, E. et al., Z. Folyoirat, vol. 77, pp. 294–298, (1971).
Kissinger, P. T. et al., Anal. Letters, vol. 6, pp. 465–477, (1973).

*Primary Examiner*—G. L. Kaplan

[57] ABSTRACT

A flow-through electrochemical cell distinguished by the feature of a working electrode comprising selected carbon black powder(s) dispersed within an inert binder. An outstanding characteristic of the invention is the markedly improved signal/noise ratio of the electrode which enables a significant gain in the sensitivity level at which trace compounds can be detected. As an example of utility, as little as 5 to 30 parts per billion (ppb) of most phenolic compounds in water can be determined by liquid chromatographic separation of species and amperometric electrochemical detection, using the described flow-through cell to monitor the column effluent. No sample preparation is required.

15 Claims, 6 Drawing Figures

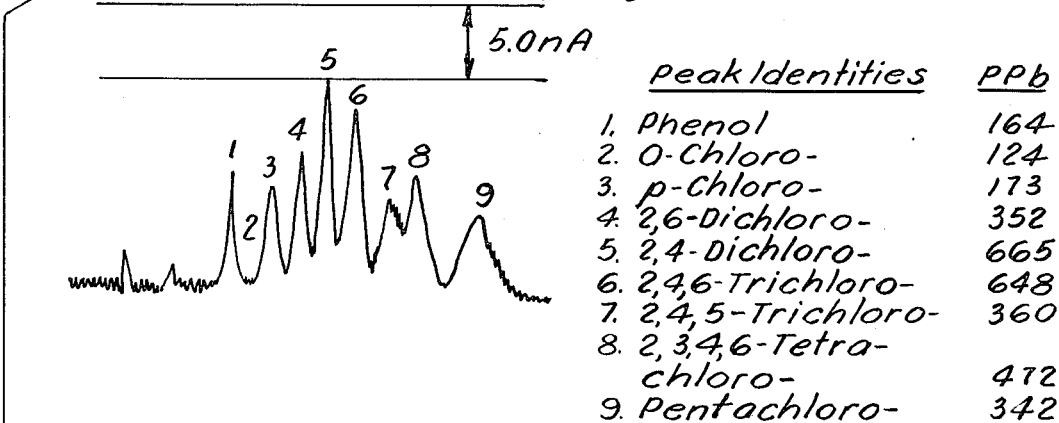
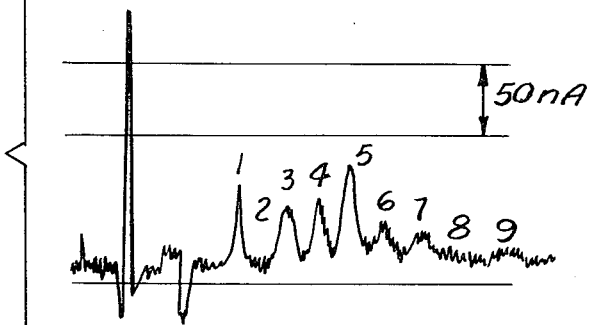
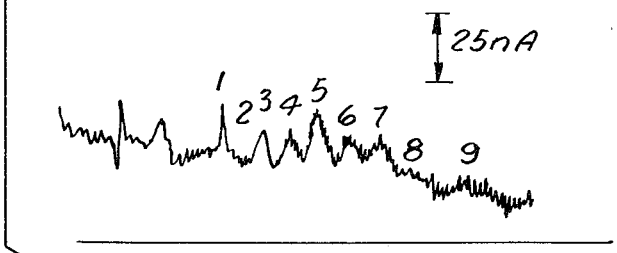
Fig. 3

CHROMATOGRAPHY APPARATUS WITH ELECTROCHEMICAL DETECTOR HAVING CARBON-BLACK CONTAINING WORKING ELECTRODE

This is a continuation of application Ser. No. 870,554 filed January 18, 1978 and now abandoned.

FIELD OF THE INVENTION

The invention relates to the field of electrochemical detection and quantitative analysis of trace electro-oxidizable and reducible species, and is particularly advantageously adapted for the electro-oxidizable mode. More specifically, the invention relates to liquid chromatographic separation techniques with continuous, improved electrochemical detection of the effluent species.

BACKGROUND OF THE INVENTION

The amperometric electrochemical analytical technique, in its classical aspects, concerns the isolation and measurement of faradaic electron transfer currents of a chemical species undergoing electro-oxidation or electro-reduction in a dilute solution of the species. The technique utilizes the principle of masking of the electrical force field where the species carries a charge. This is typically accomplished by introducing a supporting electrolyte into the solution, which because of its dominant presence, effectively eliminates migration of the species due to the electrical force field attraction. Under ideal conditions, therefore, and after the layer of species adjacent to the electrode is depleted, a stabilized current flow is established which is limited by the rate at which the species diffuses into the depleted zone. Thus, the diffusion rate and hence the current is a function of the concentration gradient driving force, and its value thus may be used to deduce species concentration. The case is more complex for a flowing stream, but under the conditions of laminar flow, a mass transport diffusion rate is achievable that correlates well with species actual concentration. Further, since chemical species oxidize or reduce at characteristic potentials, the principle may also be applied to derive qualitative species identification information, using curve interpretation, for example, with voltametric scanning.

Since solvent systems begin to respond at other than low applied potentials, and thus produce non-species specific interferences, the working potentials generally are not large for any system. The most sophisticated electrochemical detector systems, for example, work approximately in the −2.5 volt to 0 volt range for the electro-reducible mode (cathodic polarization range), and from about 0 to +1.5 volt, for the electro-oxidizable mode (anodic polarization range).

Adequate sensitivity for trace analysis is also critically dependent on electrode selection. In this respect, relatively few electrode matrials are known to have satisfactory utility. Moreover, while it has been mentioned that thin layer phenomena under laminar flow conditions produces a stable boundary layer, making the electrochemical detection technique potentially applicable to the monitoring of flowing sample streams (as in the case when used with a chromatographic column), this further sophistication has been of generally narrow practical application because of electrode design and material problems.

In respect to specific systems, the classical dropping mercury electrode (DME) is with but a few exceptions limited to the electro-reducible mode of analysis (−2.5 to 0 volt), and is hence usually unsatisfactory for a large class of organic compounds that are electro-oxidizable, but not electro-reducible. There are rare exceptions of compounds that oxidize in the cathodic potential range, but these compounds are so infrequent as to permit the above generalization. Also, while a few literature publications have indicated limited success in adapting the DME electrode to continuous flow analysis, the conversion is generally considered unsatisfactory and little, if at all, used in the practical sense especially for trace analysis. Thus, the DME electrode is almost entirely confined to use with non-stirred solutions.

Noble metal electrodes have sometimes been considered for use in electrochemical analysis but are extremely prone to the formation of metal oxide films with consequent surface fouling problems. Also, there is little likelihood that the narrow potential working range of the noble metals would be considered entirely satisfactory even if surface fouling problems could be controlled acceptably.

Carbon-based electrodes (usually inferring spectroscopic grade graphite) are more inherently suited for electro-oxidation analysis and may also be used for electro-reductions over a range of about ±1.5 volts. Thus, carbon electrodes would be of particular interest for electro-active species like phenolics, including halogenated phenols, which are of great concern in the environment because of their toxicity to aquatic life. However, since the early demonstration of the feasibility of electrochemical detection for methyl substituted phenols, very little further work has been reported on the oxidation of simple phenols. Reasons for this are believed found in the electrode noise and filming problems encountered when operating carbon electrodes at the higher applied potentials required to oxidize phenols compared to aromatic amines. The problems with high residual currents and detector noise at carbon anodes, for example, are well documented but the techniques for reducing the noise by impregnating the electrodes with mineral oils, wax or similar organic-soluble substances are not considered adequate for non-aqueous solvent systems. For similar reasons, the popular carbon paste anode (graphite powder in a paste medium) is generally considered unsuitable for monitoring the aqueous-organic mixtures normally required to elute the more water-insoluble compounds from liquid chromatographic columns.

The prior art has also considered the feasibility of combining graphite powders with more solvent tolerant materials. In this respect, polyethylene, Teflon ® and silicone rubbers have been specifically suggested. Such electrode forms have made little progress, however, in terms of acceptance by the art, and lack of optimum sensitivity would seem indicated. Thus reproduction of two such prior art structures using a polyethylene and also a Teflon matrix form, mixed with graphite powder, produced generally inferior signal definition characteristics, and in one case inifinite cell resistance and thus unsuitability of purpose.

SUMMARY OF THE INVENTION

The invention is the discovery that selected carbon black powders, which are conductive when dispersed in an inert binder, provide remarkable signal definition characteristics, in a durable and widely applicable electrode form, that has heretofore been genuinely sought by the art. Such electrode forms are ideally suited, for example, to continuous flow analysis, such as in conjunction with a chromatographic separating column for monitoring the effluent stream. What is particularly desirable is that the electrode may be molded to practically any shape, and thus is suitable for use in generally all types of flow-through electrochemical cell designs. Such electrodes may be heat and pressure molded into tubular shapes, for example, using common thermoforming techniques, and the flow passage of the electrode drilled out with a common metal drill bit. Without other surface preparation including no finishing preparation of the drilled critical surface, (except in some cases several or more passthroughs with a pipe cleaner) the performance characteristics of this simple electrode form has far surpassed comparable prior electrodes, including those with the most sophisticated and laboriously prepared surfaces. For example, there is no comparable electrode known in the prior art capable of measuring the presence of trace halogenated phenol in water streams, on the order of magnitude achieved by the simply prepared electrode design of the present invention. In addition, such electrodes may be used repeatedly, and over long operating periods without irreversible surface deterioration or fouling problems. The effective working life of such electrodes in fact, using normal precaution to avoid contact with too high a concentration, appears practically indefinite at this time using simple overnight electrode soaking in a suitable solvent to rejuvenate the electrode for each subsequent day's analyses. Also, because the electrode is susceptible to practically any configuration, it may be designed for easy accessibility and replacement in terms of but a few minutes to remove and install a fresh working electrode. In addition, generally good reproducible data is generated between the original and the replacement electrode. And importantly, there appears to be little if any serious limitations as to the selection of the preferred solvent system, a feature for carbon electrodes that is believed unique in the prior art when coupled with high sensitivity for difficult chemical species.

Carbon black as the term is used herein means finely divided forms of carbon or carbon powders of preferably about 10 to 100 millimicrons, average particle size, made by the incomplete combustion or thermal decomposition of natural gas or petroleum oil or the equivalent carbonaceous starting material. The principle types, according to the method of production, are channel black (also called impingement black), furnace black, and thermal black. Furnace blacks are the most preferred species. The claims at the end of the specification exclude, however, carbon blacks unsuitable for trace analysis of the below specified halogenated phenolics, in the mode described hereinafter. In this respect, suitability for "trace analysis" as used in this specification, and in the appended claims, means utility for detecting species concentrations at detection limits of less than 1 part per million (ppm).

Materials suitable for binding carbon blacks into a solid body of definite geometry may be used with the invention, and such materials as are intended to be covered by the scope of the invention are characterized as being non-conductive except through means of the introduction of a conductive material (i.e. conductive carbon black(s)). Known materials having utility for binding together graphite powders in the preparation of prior art graphite powder electrodes, for example, may be suitably employed as binder materials, as well, for the carbon blacks of the present invention. Moldable and heat formable synthetic resinous thermoplastic binder materials are preferred, and of this class, olefinic homopolymers and copolymers (the latter intended to cover polymers prepared from the copolymerization of two or more monomers, one of which is an olefin) are most preferred. Binders that form a smooth critical surface finish like the olefins are thus particularly desired since laminar flow is critical to stream monitoring. Waxes may also be used as a suitable binder where tolerance is found with respect to the preferred solvent system employed. Where the binder material is incapable of holding together a satisfactory quantity or concentration of carbon black, necessary to impart desired electrode properties, of course, the binder material for that species of carbon black would be considered unsuitable.

THE DRAWING

FIG. 3 illustrates reproductions of chromatograms of three carbon-based working electrodes. The upper chromatogram represents a preferred carbon black electrode form, while the lower two chromatograms are shown for comparative evaluation.

Figure 4:
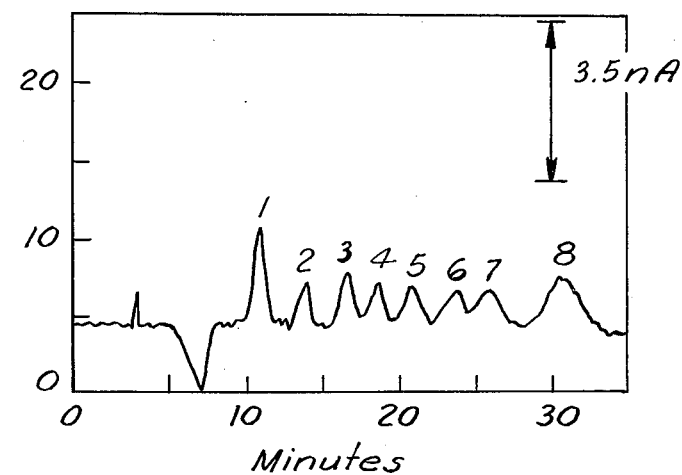

FIG. 4 reproduces an observed chromatogram for a standard mixture of phenolic species from which approximate estimations of minimal detection limits can be calculated with respect to a preferred carbon black electrode composition and design.

Figure 5:
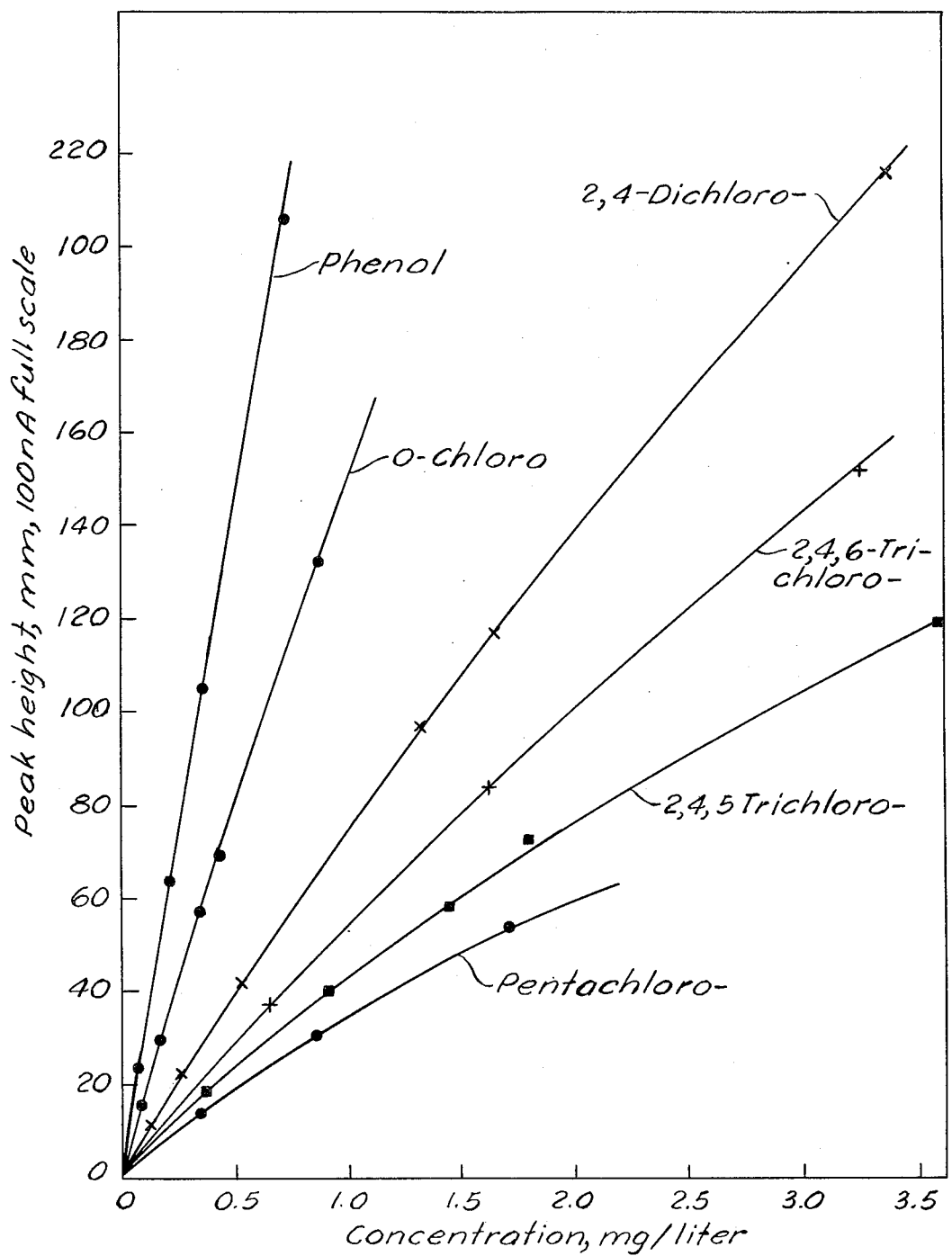

FIG. 5 shows peak height response curves for phenol and five representative chlorophenols, plotted at various species concentrations in order to show detector response linearity.

Figure 6:
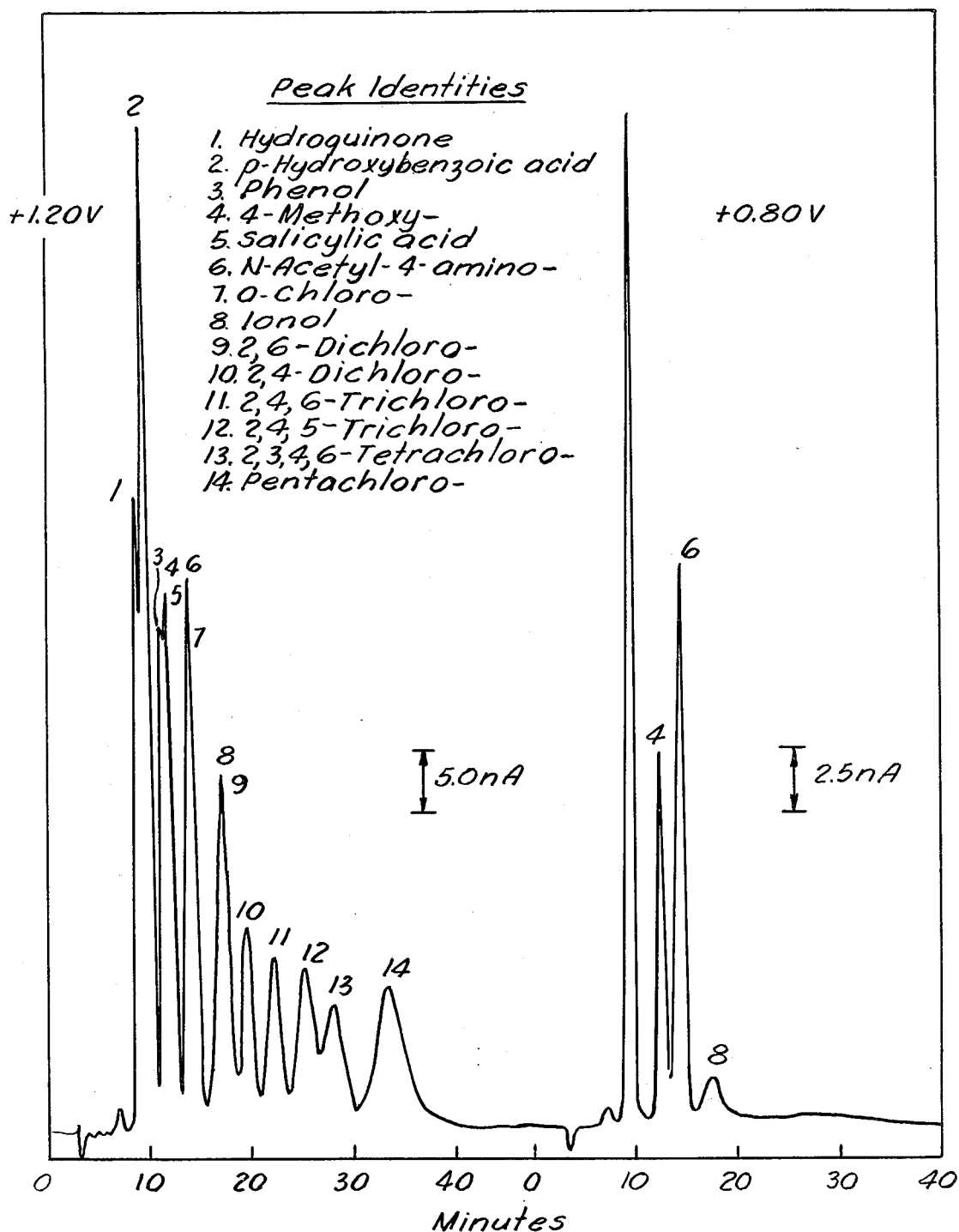

FIG. 6 reproduces two chromatograms generated simultaneously, from two electro-chemical cells, constructed according to the present teachings, and operated at distinct potentials to show selective species response.

DETAILED DESCRIPTION OF THE CHROMATOGRAPHIC ARRANGEMENT

Figure 1:
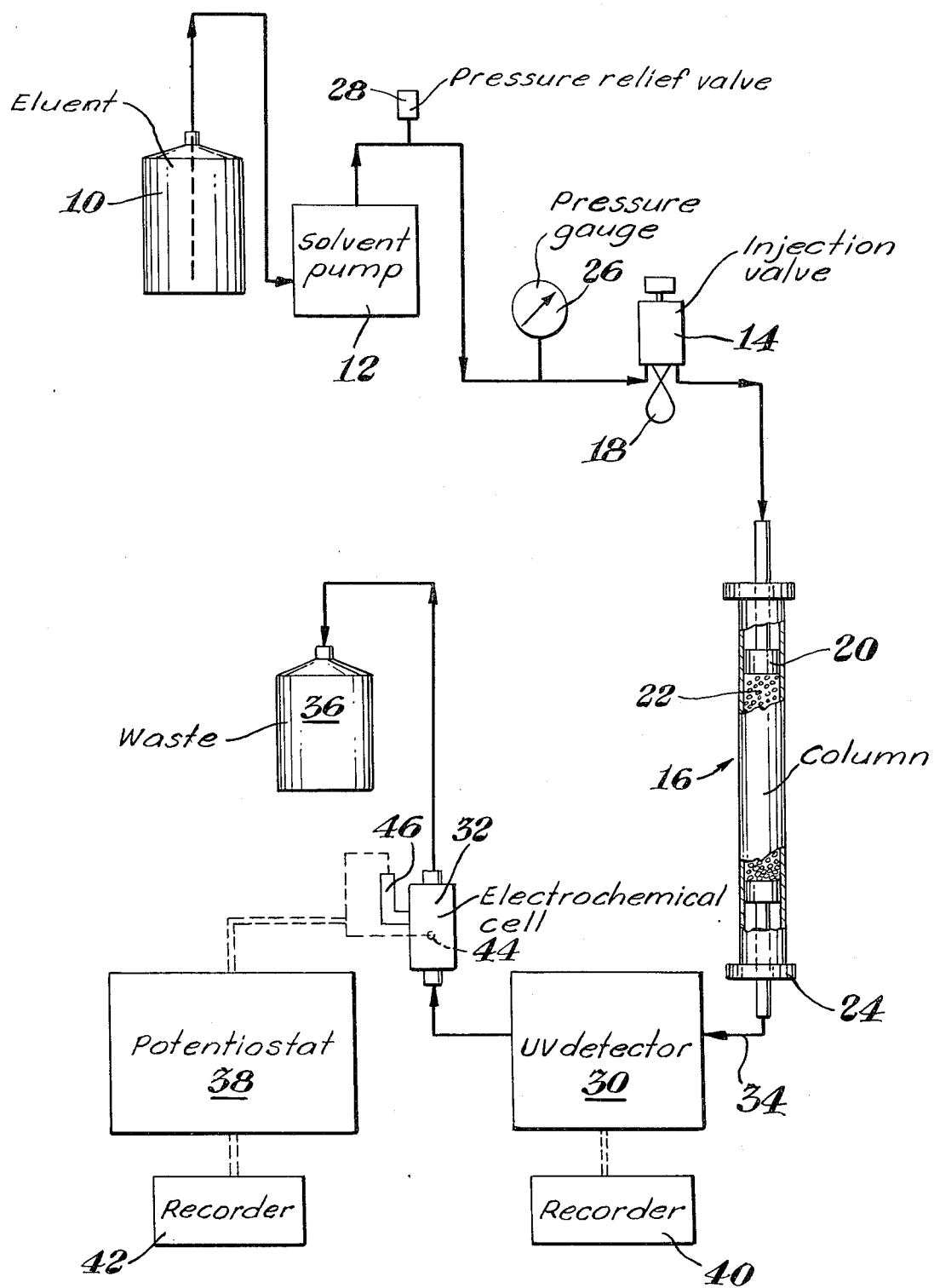
FIG. 1 is a diagrammatical view showing preferred apparatus for chromatagraphically separating species, detecting species through complementary electrochemical and UV detector systems, and for continuously displaying the signals generated by the detector systems.

In the FIG. 1 arrangement, designed specifically to detect phenolic and trace halogenated phenolic response, isocratic, preferably acetonitrile-based eluent, which has been briefly vacuum degassed, is pumped from supply bottle 10 using either a Model 6000-A pulseless pump (Waters Associates) or a Milton Roy chromatographic minipump 12, through a rotary injection valve 14, and onto a glass liquid chromatographic column 16. The pumping rate is approximately 2.0 ml/minute. An injection loop 18 of 280 µl size is employed, except where otherwise specified. The glass column from Laboratory Data Control, Riviera Beach, Fla., is 12.7 mm I.D.×330 mm, and is equipped with moveable plungers 20 to adjust the resin bed 22 to a preferred 170 mm in length. The column is slurry packed with Aminex 50W-X4, 20–30μ, strong cation exchange resin in the hydrogen ion form, from Bio-Rad Laboratories, Richmond, Calif. Modified column end fittings 24 are prepared from stainless steel to replace the less acid-resistant fittings commercially supplied.

Since the glass column is rated to withstand a maximum of 300 psi, a pressure gauge 26 is used to monitor the column pressure. A pressure relief valve 28 is provided when the Milton Roy pump is used. With the alternate pump, it is possible to use a built-in pressure limit switch to shut down if the column pressure exceeds the rated maximum.

The detector system includes an optional Perkin Elmer Model LC-55 variable wavelength UV detector 30 in conjunction with an electrochemical cell 32 using the carbon black electrode form of the present invention. A narrow bore, 0.012 inch I.D. Teflon tube 34 carries the elution solvent and sample to the dual detector system, and then to a waste bottle 36. For work with phenolic and halogenated phenolic samples, the UV detector is set at 213 nanometeers, and the electrochemical cell at +1.2 volts, using a suitable two-electrode potentiostat 38. The detector outputs are displayed on Sargent Model XKR recorders 40, 42 set to give 0.04 absorbence units full scale for UV absorbence output, and 20 to 100 nanoamperes (nA) full scale for the electrochemical output. Occasionally, the UV detector is removed from the arrangement. The only effect on the electrochemical detector response is a slightly increased susceptibility to occasional current spikes which suggests that the UV detector is helping to ground the liquid chromatographic system.

The instrument preferred for the potentiostat is a Model PR-10-LC, from LEDLAND INSTRUMENTS, Lansing, Mich. (also described in U.S. Pat. No. 3,922,205). The working electrode 44 is held at virtual ground and the instrument permits an adjustable potential of from between 0 to ±2.0 volts to be applied between the working electrode vis a vis the reference electrode 46. The potentiostat current output at nominally 0–1 or 0–10μ amperes (μA)/volt can be adjusted from 0–1 nanoamperes (nA) to 0–1μ A full-scale response with the appropriate variable range recorder.

Since this instrument is designed for classical polarographic measurements (from 0 to −2 volts impressed voltage) suitable but relatively simple modifications are required to convert the instrument to operate in the above-described mode. To do this, the initial voltage is connected to a bipolar power supply, as is the potentiometer for adjusting the sweep direction. Also, since the current through the cell can be operated in the reverse direction (to that of polarographic measurements) the leads to the digital voltmeter, if mono-tonic, are appropriately switched to accommodate the reversal in the sign of the D.C. voltage measured. These modifications are currently made available on the PR-10-LC Model instrument, as purchased.

Electro-Chemical Cell

Figure 2:
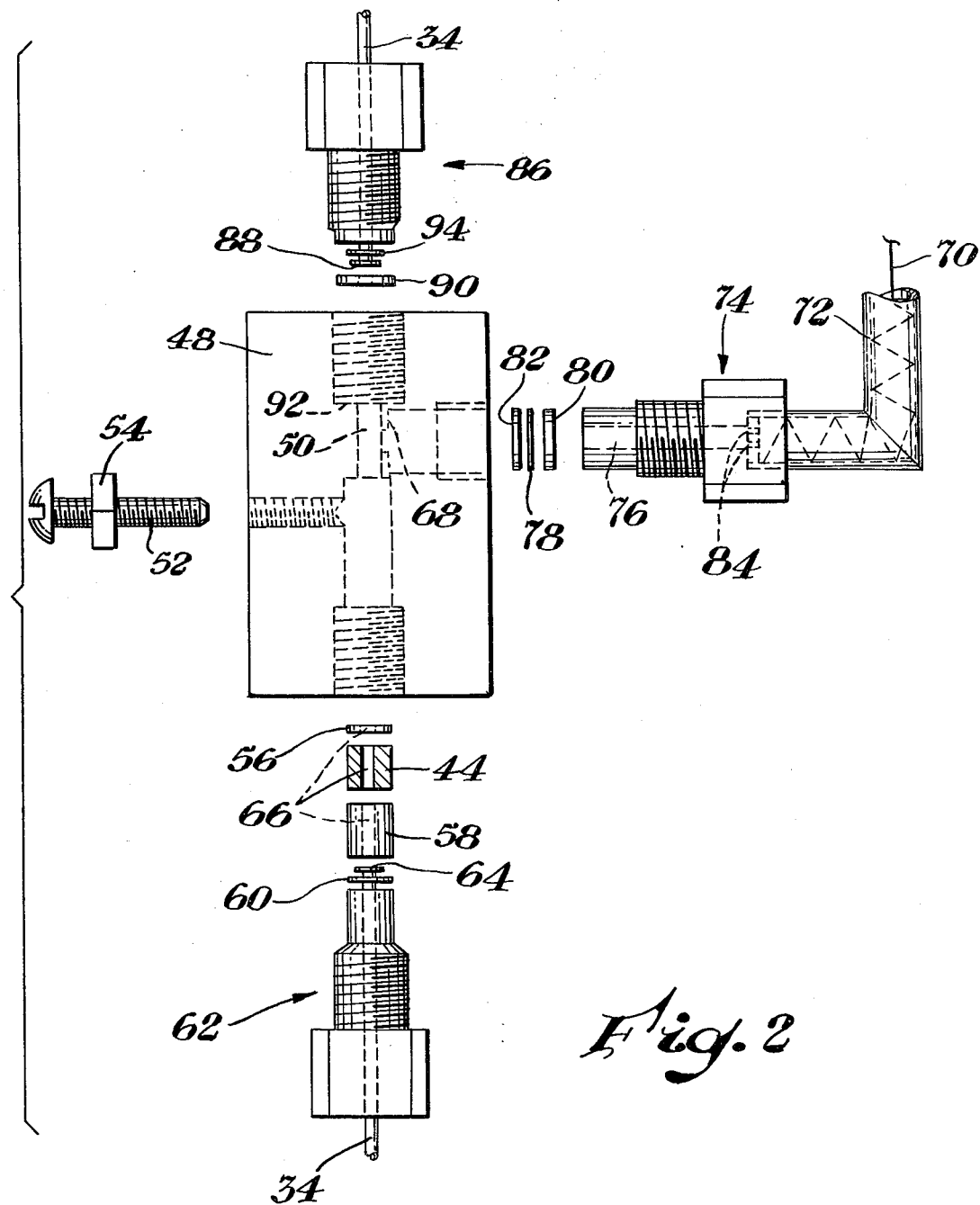
FIG. 2 is an exploded view of a preferred electrochemical cell design which may advantageously feature the improved working electrode of the present invention.

The design of the electrochemical cell most preferred for use with the invention is shown in FIG. 2 (also see Mason et al., Anal. Chem. 42, 548 (1970) incorporated by reference).

The cell uses a cell body 48 of fluorocarbon plastic (product trade designation "Kel-F" from 3M Corporation). The tubular shaped working electrode 44, aligned with its bore vertical, abuts a vertical discharge passage 50 defined in the cell body. A brass or copper screw 52 which enters the side of the cell body is in pressed contact against the side of the working electrode, and provides means to attach the lead from the potentiostat. A tightening nut 54 is used to fix the position of the screw.

The working electrode is firmly held between a Teflon spacer 56 which seats against an internal step, and a second Teflon spacer 58. The latter is seated against a metal washer 60, and the entire assembly is placed under compression by a threaded Teflon plug 62 whose forward end provides snug seating compression against the assembly through washer 60. A Teflon tube, previously given Reference No. 34, passes through plug 62, and employs a flanged end 64 which is disposed in a leak-tight seating arrangement between washer 60 and Teflon spacer 58. It is essential that the bore 66, formed cooperatively by elements 44, 56 and 58, is perfectly aligned to promote laminar flow of the effluent sample entering from the column through tube 30.

The reference electrode 46 comprises a wire 70 of silver chloride coated on a core of silver and immersed in aqueous 1.0 M lithium chloride solution, and is contained in a glass tube 72. The tube is fixed by glue into the recessed end of a Teflon plug 74 which is threadably secured in the side of cell body 48. The plug defines a horizontal bore 76 which communicates with the sample discharge passage 50 of the cell body through a suitable dialysis membrane 78 (cellulose acetate being preferred for this study). The membrane 78 is fixedly held between Teflon spacers 80, 82, the former of which is seated with an internal step 68, and the latter of which is seated with the forward end of plug 74. The lithium chloride cavity hence extends backward from the dialysis membrane, through bore 76, and into communication with the Ag/AgCl reference electrode through openings 84 in glass tube 72.

A third Teflon plug 86 is threadably fastened to the top of the cell body in alignment with the central discharge passage. A Teflon tube, also given Reference No. 34, extends vertically through plug 86, and includes a flanged end 88, which is seated in tight leak-resistant arrangement between the forward end of plug 86 and a Teflon spacer 90. A metal washer 94 is disposed between flanged end 88 and plug 86. The Teflon spacer is, in turn, seated against an internal step 92. Column effluent thus flows up through the central eluent passage 50, past the dialysis membrane and exits via the plug 86 assembly to waste bottle 36.

Preparation of the Working Electrode

The cell design, supra, utilizes a working electrode of 3/16 inch O.D.×3/16 inch axial length, with a 1/16 inch internal bore. In most cases in these studies, the working electrodes are prepared from commercially available pellets of precompounded carbon black-thermoplastic which after a pre-grinding step, are thermoformed to rough dimensions, followed by machining and drilling procedures to achieve suitably precise dimensions. In a few instances, electrodes are prepared by compounding carbon blacks with selected binder materials.

The preparation of suitable electrodes from precompounded materials commences with the grinding of the pellets into relatively fine particles, carried out in the presence of liquid nitrogen. A (Labconco) laboratory grinding mill is suitable, adjusted to the finest setting. The ground material in 20–25 gram batches is then allowed to dry thoroughly for 3 to 4 hours under draft in a laboratory vacuum hood. The ground powder suitably dry may be then thermoformed using matched platen dies. The preferred forming dies use a flat plate matched to a plate defining a series of cavities each 6 inches by ⅛ inch radius (thus forming rods of half cylinder geometry). The ground powder is poured into the cavities, allowing for a slight overfill. The dies are then matched and snugged together in a suitable press, and preheated for 15 minutes to bring the temperature of the powder to a generally uniform 200°–225° C. This is followed by application of 30 tons ram pressure for 3 minutes to fuse the particles into the half cylinder rod shape, followed by about 10–15 minutes of holding time to assure sufficient cooling. In some cases (as designated hereafter) further powder is applied to fill the slight depression left on the flat side of the half cylinder rods, and the procedure repeated. Such electrodes are distinguished below by the designation pressed 2X.

Simultaneously with the preparation of the half cylinder rods, using a dual station press, powder is placed between aluminum foil, in sandwich form, and the sandwich is pressure and heat formed between matched flat dies to prepare flashing material.

A pair of half cylinders, with the flashing material laid in between are then brought together, and joined by heat and pressure to form carbon black filled rods of approximately 6 inches by ¼ inch diameter. In practice, a splittable die with 16 half cylinder cavities is separated and the two die halves brought together, with the flashing in between, thus preparing eight rods. Each cycle uses 10–15 minutes of preheat time controlled at about 200°–225° C., 3 minutes of press time and about 10 minutes of cooling time. The rods are subsequently turned on a lathe to obtain a more precise external dimension, cut to 3/16 inch axial length, and the central bore is drilled using a common 1/16 inch metal drill bit. Drilling speed is critically controlled between maximum and minimum drill speed limits, to insure that the bore surface is of optimum smoothness. Melting phenomena is believed to contribute to the extremely smooth surface achieved by this expedient preparation process.

Working electrodes prepared by compounding carbon blacks with thermoplastic binders utilize the same preparation steps except the pre-grinding step is not required. The carbon black and binder material are compounded in the presence of carbon tetrachloride maintained at its boiling temperature of 74° C. A 600 cc beaker is employed which is inserted into a 600 cc heating mantle. Thermoplastic and a half portion of the desired amount of carbon black powder are added to the beaker, and the solution stirred continuously. The second half portion of carbon black is later added, and the solution replenished with further carbon tetrachloride solvent, as required. The beaker is then moved to an ultrasonic bath (H$_2$O) with the water at room temperature. Stirring is continued until the solution cools to room temperature. The resulting material in the form of a gel is poured into a baking dish (in a vacuum hood enclosure) and residual solvent evaporated until the gel shows the formation of cracks. The material is then stirred with a spatula, until it reaches a crumbly consistency, and is then forced through a 12 mesh sieve, and allowed to stand for 16–24 hours to air dry. Following further drying under vacuum for 24 hours, the material is ready to be pressure formed into rods by the described procedure.

Carbon Black Vs. Comparative Carbon Based Electrode Compositions

Various different types of carbon based electrodes are constructed for comparative evaluations for phenol and halogenated phenol response using the described electro-chemical cell. Example 1, below, is a carbon black electrode form covered within the scope of the invention. Comparative Examples 1–6 are various different carbon based electrode forms. Those of the Comparative Example electrodes considered experimental, and not necessarily a part of the prior art, are marked by an asterisk (*). Specific electrode compositions and methods of preparation are:

Example 1 Furnace-Black Carbon/Polyethylene

Prepared from precompounded pellets containing 50 percent furnace-black carbon and 50 percent polyethylene, by weight, available as a color concentrate from Ampacet, Mount Vernon, N.Y. The pellets are sold under product code designation no. 19270 (see Ampacet Trade Bulletin 12-76, entitled "Ampacet Film and General Purpose Color and Additive Concentrates").

Comp. Ex. No. 1* Graphite Powder/Polyethylene

Prepared from microparticular graphite, from Ultra Carbon Corp., Bay City, Mich., compounded with an equal weight of high pressure, low density, polyethylene. Graphite powders of average particle size 1 and 74 microns are used. Only data with respect to the former, however, is reported since electrodes employing the larger particle size measure infinite resistance.

Comp. Ex. No. 2 Graphite Powder/Teflon

Prepared from commercially available graphite-filled Teflon rods by machining. One sample contains 25 percent graphite in Teflon and the other, obtained from Dixon Corp., Bristol, R.I., is 35 percent graphite. Only the results with the more efficient 25 percent graphite/75 percent Teflon electrode composition are reported.

Comp. Ex. No. 3* Graphite/Nujol

Prepared from graphite rod, trade designation U-7, from Ultra Carbon Corp., by machining to the proper dimensions. The inner bore is polished with 60-mesh Alundum powder. After rinsing the polished electrode with petroleum ether (30°–600° C.), ethyl acetate, and methanol, the electrode is air-dried and immersed in Nujol mineral oil under vacuum for about 60 minutes. Excess Nujol is removed from the impregnated electrode with a tissue and a jet of dry air.

Comp. Ex. No. 4* Graphite/Phenol-Formaldehyde

Prepared from U-7 graphite rod which is polished as described above and impregnated under vacuum for about 60 minutes with a mixture of phenol-formaldehyde monomers, and polymerized in situ. Following the polymerization, a second polishing step is applied to the critical electrode surface.

Comp. Ex. No. 5* Graphite/Styrene-Divinylbenzene

Prepared from polished U-7 graphite rod which is impregnated under vacuum with a mixture of 9:1 styrene:divinylbenzene monomers. Subsequent polymerization of the monomers in situ is performed in a heated sealed ampoule, and the electrodes are subjected to a post polishing step.

Comp. Ex. No. 6 Vitreous Carbon

A vitreous carbon electrode of the proper dimensions for the electrochemical cell is custom prepared by the Tokai Electrode Manufacturing Company of Japan. The electrode's internal surface is not polished.

Electrode Evaluations

Each of the seven different types of electrodes, supra, is installed in a detector cell body and evaluated in the liquid chromatographic system by analyzing standard mixtures of phenol and chlorophenols at +1.20 V versus Ag/AgCl. To compare data obtained with various electrodes, chromatographic peak heights equivalent to 1 mg/liter (1 ppm) are used to calculate signal-to-noise ratios for each compound tested. The results are listed in Table I.

usefulness of the phenol/formaldehyde treated anode is severely limited because of a very high residual current.

Also, in FIG. 3, chromatograms for three of the electrodes tested under similar experimental conditions are shown to emphasize the dramatic improvement in response of the higher chlorinated phenols on the furnace-black carbon/polyethylene electrode. Note that to produce measurable chromatographic peaks the concentrations of standards used for the graphite/Teflon electrode evaluation are 2.5 times larger than those for the other electrodes.

The vitreous carbon electrode is entirely unsuitable because of extreme noise and is only briefly examined. While polishing of the critical surface would be expected to improve the performance of the vitreous carbon electrode, the technique is considered unattractive because of the extreme hardness of the material and is

TABLE I
PHENOLIC RESPONSES FOR VARIOUS CARBON ANODE COMPOSITIONS
Signal/Noise per Part Per Million Phenolic

|  | Full-Scale Response $\mu A$ | Phenol | 2-Cl | 2,4-$Cl_2$ | 2,4,6-$Cl_3$ | 2,3,4,6-$Cl_4$ | $Cl_5$ |
|---|---|---|---|---|---|---|---|
| 50% Carbon Black in Polyethylene | 0.10 | 360 | 200 | 120 | 80 | 70 | 60 |
| 50% Graphite Powder in Polyethylene | 0.10 | 210 | 100 | 55 | 30 | 9 | 8 |
| U-7 Graphite/Nujol Coating | 1.0 | 220 | 120 | 60 | 25 | 9 | 5 |
| 25% Graphite in Teflon | 0.50 | 30 | 12 | 10 | 4 | 2 | 2 |
| U-7 Graphite/Phenol-formaldehyde Coating | 1.0 | 45 | 30 | 10 | 6 | 4 | 4 |
| Vitreous Carbon[1] | 0.5 | 35 | 20 | 10 | 4 | — | — |
| U-7 Graphite/Styrene-Divinyl-benzene Coating | 0.20 | — | 20 | 10 | 6 | — | — |

[1]Vitreous carbon applied potential is only +1.10 V versus Ag/AgCl.

As the tabulated data verifies (from Table I, supra) the Example 1 furnace-black/polyethylene electrode achieves a marked signal definition superiority, with respect to all Comparative Examples and particularly with the difficult tetrachloro- and pentachlorophenol species.

The most effective Comparative Examples, Graphite/polyethylene and Nujol-impregnated graphite electrodes, are judged adequate for phenol through the dichlorophenols, but results failed badly for the higher chlorinated phenols compared to the carbon black electrode of Example 1. In addition, frequent regeneration of the Nujol-impregnated electrode is required. The not attempted for this experiment.

Modified Carbon Black Electrode Forms

In order to reaffirm the data above, various different carbon black electrodes are examined for signal/noise ratio characteristics with respect to phenolic and halogenated phenol response. The Example 1 electrode is included, as well, in these studies. Chromatographic conditions are varied somewhat. For example, an Altex Model 110 chromatographic pump is substituted, and flow rate and column pressure is adjusted downwardly. None of the changed conditions are considered to significantly affect the results. The data is presented in Table II, below.

TABLE II

| Ex. No. | Composition by wt. % (Carbon Black given first) | Product Code No. Fabrication | Phenol | 2-Cl | 2-6 $Cl_2$ | 2,4,6-$Cl_3$ | 2,3,4,6-$Cl_4$ | $Cl_5$ | Cell Resistance (ohms) | Equilibration Time (Minutes) | Average Particle Size (Millimicrons) |
|---|---|---|---|---|---|---|---|---|---|---|---|
| 1 | 50/50 PE | Code No. 19270 | 380 | 190 | 200 | 120 | 70 | 60 | 4–6 K | 20–30 | 50–75 |
|  |  |  | 410 | 200 | 170 | 100 | 50 | 50 | 4–6 K | 20–30 | 50–75 |
| 1(a) | Same | Code No. 19270 | 830 | 430 | 370 | 190 | 100 | 80 | 4–6 K | 20–30 | 50–75 |
|  |  | Pressed 2 × | 800 | 400 | 360 | 190 | 90 | 70 | 4–6 K | 20–30 | 50–75 |
| 1(b) | Same | Code No. 19270 |  |  |  |  |  |  |  |  |  |
|  |  | Pressed 2 × Polished | 270 | 200 | 220 | 160 | 110 | 110 | 4–6 K | 20–30 | 50–75 |
| 2 | 40/60 | Code No. |  |  |  |  |  |  |  |  |  |

TABLE II-continued

| Ex. No. | Composition by wt. % (Carbon Black given first) | Product Code No. Fabrication | Phenol | 2-Cl | 2-6 Cl$_2$ | 2,4,6-Cl$_3$ | 2,3,4,6-Cl$_4$ | Cl$_5$ | Cell Resistance (ohms) | Equilibration Time (Minutes) | Average Particle Size (Millimicrons) |
|---|---|---|---|---|---|---|---|---|---|---|---|
|  | PE | 19200 Pressed 2× | 70 | 40 | 60 | 50 | 40 | 40 | 25 K | 60 | 50-75 |
| 3 | 25/75 PE | Code No. 49316 Pressed 2× | 20 | 15 | 13 | 14 | 12 | 13 | 11 K | 60 | 25 |
| 4 | 35/65 PP | Code No. 49326 Pressed 2× | 40 | 25 | 30 | 20 | 13 | 13 | 40 K | 50 | 25 |
| 4(a) | 35/65 PP | Code No. 49236 Pressed 2× Polished | 80 | 55 | 55 | 40 | 40 | 40 | 15 K | 40 | 25 |
| 5 | 55/45 EVA | Code No. 19258 Pressed 2× | 100 | 40 | 50 | 50 | 40 | 30 | 7 K | 180 | 50-75 |
| 5(a) | 55/45 EVA | Code No. 19258 Pressed 2× Polished | 980 | 530 | 470 | 290 | 190 | 180 | 7 K | 180 | 50-75 |
| 6 | 40/60 PP | Code No. L-7068(f) Pressed 2× | 360 | 180 | 160 | 80 | 45 | 40 | 5.5 K | 180 | 25 |

In construing the data presented in Table II, pressed 2× refers to the method of fabrication as discussed previously. The abbreviations PE, PP, and EVA refer to the synthetic plastics polyethylene homopolymer, polypropylene homopolymer, and ethylene-vinyl acetate copolymer, respectively. The electrode bores are unfinished except where specified otherwise. In all cases where polishing is practiced, the same consists of the minimal polishing effect provided by several pass throughs of a pipe cleaner, except for Example No. 4(a). In this instance polishing is effected in a like manner, but with the assistance of alumina, 0.3 micron particle size, polishing abrasive. Rotational movement is avoided in order to avoid any impression of a grain in the bore, at right angles to the direction of flow.

In comparing relative performance, it should also be taken into account that the sensitivity of the electrode is calculated based on peak heights as opposed to peak areas. Thus, the figures in the vertical columns may be validly compared, but not so with the figures across the page. Thus, the sensitivity of the Example 1 electrode for phenol (380, reported value) as compared to pentachlorophenol (60, reported value) cannot be validly employed to support the conclusion that the electrode is more sensitive to the phenol species. This is because of spreading of the later eluted pentachloro species, that obviously lessens species peak height, solely because of typical liquid chromatographic phenomena.

Given the sample concentrations, however, the suitability for trace analysis of all electrode forms reported in Table II is obviously deducible. The standards are as follows:

| Species | Concentrations |
|---|---|
| Phenol | 98 ppb |
| 2-Cl— | 110 ppb |
| 2,6-Cl$_2$— | 206 ppb |
| 2,4,6-Cl$_3$— | 300 ppb |
| 2,3,4,6-Cl$_4$— | 436 ppb |
| Cl$_5$— | 505 ppb |

Thus, looking at the pentachlorophenol response of the Example No. 4 electrode, and knowing the species concentration of the standard is 505 ppb, the sensitivity of the electrode for that specific standard (as measured by signal/noise ratio) would be between 6 and 7, and thus quite obviously adequate for trace analysis work.

What is perhaps the most unexpected feature of the invention in addition to the excellent sensitivity observed for phenols generally is the seemingly heightened response achieved for the higher chlorinated phenols. This is dramatically evidenced particularly looking at the data generated for Example 4(a), and appears entirely contrary to the trend of carbon based electrodes generally observed with respect to Comp. Ex. 1-6, supra.

Also it appears proper to draw the conclusion that the precise binder material shows little perceptive effect on sensitivity performance. Alternatively, the concentration of the carbon black, at least so far as these binders, is beneficially high. Thus, the most optimum sensitivity is exhibited by Example No. 5(a) (55% carbon black), and secondly by the 50/50 mixtures (Examples Nos. 1-1(b)). Similarly, the least sensitive electrode is that with the least concentration of carbon black, Example No. 3. The variance in average particle size, however, does not appear to establish a trend one way or the other.

It is also significant to note that the manner of fabrication can dramatically increase sensitivity, all other variables being the same. Thus, roughly a two-fold performance gain is shown between Examples 1 and 1(a), the latter having been subjected to the second pressing step (as described above with respect to electrode preparation techniques). The effect of bore polishing on the other hand shows no consistent trend, but nevertheless oftentimes shows a very observable effect on electrode performance (compare otherwise equivalent electrodes 5 and 5a, for example).

Also, as has been previously mentioned, the Example 1 electrode form is reported in both Tables I and II, and the correlation of the data considering the kind of measurements made is considered excellent.

Not all carbon blacks may perform as admirably as those tested. Carbon blacks differ, of course, in respect to the manner of preparation, and in terms of carbon purity. Oxidation or reduction of impurities in the carbon black or binder material would, of course, contribute to high background signal. While this is observed with regard to all carbon black electrode forms within a relatively short time, as reported under the column "Equilibrium Time" in Table II, the initial high residual background interference decays to a relatively minor value. With two electrode forms, this phenomena, however, is not observed. One comprises a 50% by weight mixture of carbon black (average particle 25 millimicrons) in a polypropylene homopolymer binder. This electrode form would generally be predicted to be more suitable than Example No. 4(a), based on observations with respect to the carbon black concentration. However, the residual background current does not show the typically observed decay, even though excessive equilibration time is allowed, and thus further activity with respect to this electrode is not pursued. Similar results are observed with respect to an electrode prepared from 20% Ketjenblack ®/80% polyethylene. This performance, however, is not entirely to be unexpected since Ketjenblack is considered unique and set apart in properties from more typical carbon black species (see, for example, Product Data Bulletin No. 75-9, from Armak Company, Burt, New York).

In respect to a third electrode form of 50% channel black/50% polyethylene, average particle size 16 millimicrons, while the black is found conductive apart from the binder, the finished electrode is non-conductive. This phenomena, however, is found generally atypical among the carbon black electrode forms examined, and its cause has not been definitely assigned.

Estimation of Detection Limits

Using the Example 1 electrode form, FIG. 4 shows a chromatogram for a very dilute standard mixture of phenols from which estimates for detection limits can be calculated. For this chromatogram, the sample volume is increased from 280 $\mu$l to 520 $\mu$l, and a standard mixture containing 10 to 29 ppb of various phenols is injected. The recorder response is 35 nA full-scale. The calculated concentration of each phenol required to produce a signal-to-noise ratio of two is listed in Table III. Computed values range from 3 ppb for phenol to 17 ppb for 2,4,5-trichlorophenol. The eluent used in the detection limit study is 28% acetonitrile by volume in $H_2O$ with 0.05 N $H_2SO_4$ to suppress ionization of the phenol standards.

TABLE III[1]

DETECTION LIMITS OF SELECTED PHENOLICS
Signal/Noise = 2, 520 $\mu$l Injection, 35 namp full scale, +1.20 volt

|  | Concentration, ppb |
|---|---|
| Phenol | 3 |
| o-Chlorophenol | 6 |
| 2,6-Dichlorophenol | 8 |
| 2,4-Dichlorophenol | 9 |
| 2,4,6-Trichlorophenol | 13 |
| 2,4,5-Trichlorophenol | 17 |
| 2,3,4,6-Tetrachlorophenol | 14 |
| Pentachlorophenol | 15 |

[1]Pumping rate = 2.0 ml/min
Column bed = 12.7 × 170 MM
Bed Packing = Aminex 50W × 4, cation exchange resin, 20–30 micron particle size.

Since pulsing from the liquid chromatographic pump is considered responsible for most of the detector noise, the above computed sensitivity of the carbon black electrode while judged excellent for all species is considered conservatively stated by these specific tests.

DETECTOR RESPONSE LINEARITY

Peak-height response curves for 280-$\mu$l injections of phenol and five chlorophenols using the amperometric detector and the Example 1 furnace-black carbon/polyethylene electrode are shown in FIG. 5. Though the curves for all but phenol show some nonlinearity at concentrations below 1 ppm, the nonlinear behavior is not very pronounced. Care is exercised, however, when concentrations above 1 ppm are measured. Of these phenols tested, the 2,4,5-trichloro-, tetrachloro-, and pentachloro compounds gave standard curves with the greatest deviations from straight lines. Since the deviation is obviously predicted by the curve generated, it, of course, may be easily corrected for where that degree of precision is required.

Selection of Optimum Detector Working Potential and Series Operation

In the aforegoing evaluations, it is surmised that all compounds but phenol begin to approach a current plateau at potentials less than +1.20 volts (for the Example 1) carbon black electrode versus Ag/AgCl. Though higher potentials would be expected to yield increased response, the applied potential of +1.20 v is chosen for continuous effluent monitoring as the best approximation for achieving maximum phenolic response and minimum residual current noise. Nevertheless, various phenolic species oxidize at significantly lower potentials than +1.20 V; and thus additional detector specificity for these compounds can be obtained by lowering the applied potential to +0.80 V, for example. The more easily oxidizable phenols would include dihydroxybenzenes, methoxyphenols, Ionol, and N-acetyl-4-aminophenol.

Since only a small fraction of an eluting phenol is oxidized at the working electrode, it is thus possible to place more than one detector in series and monitor at various applied potentials to obtain the higher specificity desired. FIG. 6 shows two chromatograms obtained simultaneously from two detectors attached in series to the outlet of the UV detector. The potential on the first electrode is +120 V and on the second +0.80 V versus Ag/AgCl. Only the more easily oxidized phenols respond at the second electrode whereas all respond at the first. As the extremely good signal definition verifies, the invention is highly compatible and advantageously applied to multiple step application of discrete operating potentials. No apparent interferences between the adjacent detector systems is observed.

Detector Maintenance, Stability and Lifetime

Proper maintenance of the carbon black electrode form requires little tedious labor. Essentially rejuvenation of the cell after each day's operation requires simple water flushing techniques, and thereafter the cell is allowed to stand overnight filled with water. If high concentrations over 5–10 ppm of phenolics have reached the detector and electrode filming is evident by decreased response, 10–20 ml of N,N-dimethylformamide (DMF) may be flushed through the flow-cell to dissolve the film from the electrode.

In respect to useable lifetime, carbon-black polyethylene electrode may be used daily for long periods when the concentration of each phenolic compound to be measured is under 1 ppm or <280 ng of phenol per injection. Probable film formation on the electrode surface and serious detector sensitivity loss would be expected, however, from repeated injections of more concentrated solutions. Under normal operating conditions, detector sensitivity generally decreases at about 2 percent per hour. The sensitivity of the carbon black electrode, however, shows essentially a complete regeneration of properties using the simple overnight soaking procedure, supra.

Electrochemical Performance, Order of Elution and Response Factors for Various Species The general applicability of the carbon black electrode form to respond on an operative performance level required for trace analysis of electro-active phenolic species is shown in the Tables IV and V below. Tables VI and VII show elution times and responses for various non-phenolic species. The applied voltage to the detector using the Example 1 electrode form is set at +1.20 V, and mixed phenol standards are injected. Normalized results, all obtained on the same electrode with the same eluent strength, are tabulated. Included in the data are chromatographic column retention times and area responses on a weight and molar basis for halogenated phenols, non-halogenated phenols, and certain oxidizable carboxylic acids and other aromatic species that are found to respond to some extent.

TABLE IV

ELUTION ORDER AND DETECTOR RESPONSE HALOGENATED PHENOLS

| Compound | Retention Time, min | Area Response namp-min mg/l | Area Response namp-min μ Molar |
|---|---|---|---|
| Phenol | 11.1 | 80 | 7.5 |
| 2-Chloro- | 14.0 | 68 | 8.7 |
| 4-Chloro- | 15.0 | 73 | 9.3 |
| 2-Bromo | 15.7 | — | |
| 2,6-Dichloro- | 16.8 | 57 | 9.3 |
| 2,5-Dichloro- | 18.3 | 51 | 8.4 |
| 2,4-Dichloro- | 18.8 | 55 | 9.0 |
| 3,4-Dichloro- | 20.1 | 50 | 8.1 |
| 2,4,6-Trichloro- | 21.4 | 50 | 9.3 |
| 2,4-Dichloro-5-Methoxy- | 21.6 | 34 | 6.6 |
| 2,3,6-Trichloro- | 21.9 | 57 | 11.2 |
| 2,4,5-Trichloro- | 24.1 | 56 | 9.0 |
| 2,4-Dibromo- | 26.5 | — | |
| 2,3,4,6-Tetrachloro- | 26.6 | 43 | 10.0 |
| 2,3,5,6-Tetrachloro- | 27.2 | 60 | 13.8 |
| 2,3,4,5-Tetrachloro- | 31.1 | 47 | 11.0 |

TABLE IV-continued

ELUTION ORDER AND DETECTOR RESPONSE HALOGENATED PHENOLS

| Compound | Retention Time, min | Area Response namp-min mg/l | Area Response namp-min μ Molar |
|---|---|---|---|
| Pentachloro- | 31.6 | 62 | 16.5 |
| 2,4,6-Tribromo- | 36.3 | 28 | 9.2 |
| 2,2',6,6'-Tetrabromo-bisphenol A | 39.5 | 23 | 12.4 |

TABLE V

ELUTION ORDER AND DETECTOR RESPONSE NONHALOGENATED PHENOLS

| Compound | Retention time, min | Area Response namp-min mg/l | Area Response namp-min μ Molar |
|---|---|---|---|
| 3-Hydroxy- | 8.8 | 71 | 7.8 |
| 4-Hydroxy- | 9.0 | 58 | 6.4 |
| 2-Hydroxy- | 9.7 | 73 | 8.0 |
| 2-Hydroxy-4-tertbutyl- | 11.0 | 45 | 7.5 |
| Phenol | 11.1 | 80 | 7.5 |
| 4-Methoxy- | 11.7 | 63 | 7.8 |
| 4-Hydroxybenzaldehyde | 12.0 | 23 | 2.8 |
| 3-Methoxy- | 12.2 | 70 | 8.7 |
| 2-Methyl- | 12.4 | 85 | 9.2 |
| 4-Methyl- | 12.5 | 82 | 8.8 |
| 3-Methyl- | 12.8 | 79 | 8.5 |
| 4-tertButyl- | 12.9 | 52 | 7.7 |
| Bisphenol A | 13.5 | 52 | 11.9 |
| 4-Amino-N-Acetyl- | 13.6 | 51 | 7.7 |
| 4-Nitro- | 13.8 | 2.6 | 0.36 |
| 2-Hydroxybenzaldehyde | 14.2 | 39 | 4.8 |
| 2-Nitro- | 14.7 | 104 | 14.3 |
| 4-Nonyl- | 15.6 | 40 | 8.8 |
| Ionol | 16.3 | 31 | 6.9 |
| 2,4-Dinitro-6-secbutyl- | 17.3 | 2.3 | 0.6 |
| 2-Phenyl- | 22.4 | 78 | 13.2 |
| 4,4'-Dihydroxy-biphenyl | 24.5 | 32 | 5.9 |
| 4-Phenyl | 30.8 | 50 | 8.5 |

TABLE VI

ELUTION ORDER AND DETECTOR RESPONSE CARBOXYLIC ACIDS

| Compound | Retention time, min | Area Response namp-min mg/l | Area Response namp-min μ Molar |
|---|---|---|---|
| Oxalic | 5.0 | 0.92 | 0.08 |
| Ascorbic | 6.6 | 8.8 | 1.5 |
| Formic | 8.0 | 0.011 | 0.0005 |
| 3-Hydroxybenzoic | 9.3 | 19 | 2.7 |
| 4-Hydroxybenzoic | 9.6 | 14 | 2.0 |
| 2-Hydroxybenzoic | 11.8 | 33 | 4.5 |

TABLE VII

ELUTION ORDER AND DETECTOR RESPONSE OTHER ELECTROACTIVE AROMATICS

| Compound | Retention time | Area Response namp-min mg/l | Area Response namp-min μ Molar |
|---|---|---|---|
| 3,5,6-Trichloropyridinol | 14.6 | 19 | 3.8 |
| Styrene | 19 | 0.3 | 0.03 |
| Vinyltoluene | 23 | 2.5 | 0.30 |

In interpreting the data of the preceding Tables, it should be noted that because of the difficulties in accurately measuring the peak areas by triangulation, the response factors could have errors of about ±20%. Also, experience shows that the absolute response factors vary somewhat between different electrochemical cells, and that the relative responses are somewhat dependent upon electrode age and history. In general, however, the variation is less than a factor of two. Generalizations as can be drawn from the electrochemical detector response factors at +1.20 V presented in the Tables are:

1. The retention time of a few strongly absorbing non-phenolic species (styrene and vinyltoluene) are shown in Table VII. Styrene, vinyltoluene, 2,4-dichlorophenol, and 2,3,6-trichlorophenol are observed to respond to UV detection at 213 nm. Obviously, therefore, the UV detector is not specific for phenols, and the electrochemical detector response is required for confirmation of any observed chromatographic peaks.

2. Unless maximum precision is necessary, a single phenol standard is all that would be required for analysis of a broad variety of phenols. Thus, it will be noted that most of the phenols examined had similar molar response factors under the operating conditions employed. For example, ring substitution by electron donating groups such as -OCH$_3$, -Cl, -phenyl, -alkyl, and -OH at any position has little effect on the area responses.

3. Para substitution by electron withdrawing groups such as -NO$_2$,

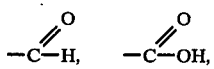

and -SO$_3$H reduces the relative responses. For example, the 4-nitrophenol and 2,4,-dinitro-6-sec-butylphenol has 15–20 times less response than phenol and 10 mg/l concentrations of 4-hydroxybenzenesulfonic acid and 3-chloro-4-hydroxybenzenesulfonic acid are not satisfactorily detectable electrochemically at +1.20 V. Thus ultimate detection limits for these kinds of compounds would thus be predicted to be generally somewhat higher in level.

4. Chlorine substitution has little effect on molar responses until four or five are present on the ring. Then, an increased molar response is observed.

In addition to the generally good response shown for phenolic species generally, related work shows analytical utility of the carbon black electrode form with respect to such electro-active oxidizable species as: aromatic amines, heterocyclic compounds and especially those containing C=N bonds, azines, certain drugs such as probucol, hydroxybenzoic acids and salts, ascorbic acid (vitamin C), antioxidants such as butylated hydroxy anisole, butylated hydroxy toluene, polymerization inhibitors such as methyl ether of hydroquinone and tertiary butyl catechol, hydroquinones, halides, sulfite, arsenite and such electro-active reducible species as Pb$^{++}$, Cu$^{++}$, quinones, and oxygen.

Generally, the carbon black electrode with the proper solvent systems finds application for performing electro-reductions and electro-oxidations over the range of about ±1.5 V, although less sensitivity is naturally expected at the extreme ends of the range. While limitations have been observed with regard to prior art carbon based electrodes, showing little utility for species that respond elegantly to the carbon black electrode form, the reverse has not been observed. Generally, the carbon black electrode is considered to have analytical utility for any species which can be electrochemically oxidized or reduced at a carbon or carbon based electrode within the indicated potential range. Preferred electro-chemical cell design is considered a matter of choice, and the carbon black electrode form, using the fabrication procedures described, is readily adapted to accommodating changes in electrode geometry.

What is claimed is:

1. Chromatography apparatus which comprises a liquid chromatography column, and as a detector for measuring electro-active sample species in the liquid effluent of the column, an improved electro-chemical cell which comprises a working electrode, a reference electrode, the working electrode communicating with a flow passageway defined by the cell whereby the liquid effluent of the chromatography column is caused to make flow contact with a surface of the working electrode, the electrochemical cell being of the type generally which detects electro-oxidizable and electro-reducible species over a potential range of about ±1.5 volts applied to the working electrode vs. the reference electrode, the improvement which comprises a working electrode of an electrically conductive carbon black powder dispersed within a generally inert, electrically nonconductive binder matrix, said working electrode being electrically conductive and characterized by suitability for trace analysis of electro-active phenolic and halogenated phenolic species generally, but not limited thereto.

2. The apparatus of claim 1 wherein said electrode comprises a furnace black powder.

3. The apparatus of claim 2 wherein the average particle size of the furnace black powder is between about 10 to about 100 millimicrons.

4. The apparatus of claim 3 wherein the binder comprises a synthetic resinous thermoplastic material.

5. The apparatus of claim 4 wherein the binder comprises an olefinic homopolymer or copolymer.

6. The apparatus of claim 1 wherein the carbon black/binder matrix composition comprises about 50 percent by weight or greater of carbon black.

7. The apparatus of claim 6 wherein the working electrode comprises a furnace black powder.

8. The apparatus of claim 7 wherein the binder comprises a synthetic resinous thermoplastic material.

9. The apparatus of claim 8 wherein the binder comprises an olefinic homopolymer or copolymer.

10. The apparatus of claim 8 wherein at least a part of said flow passageway comprises a drilled bore in the working electrode.

11. The apparatus of claim 8 wherein the average particle size of the furnace black powder is between about 10 to about 10 millimicrons.

12. The apparatus of claim 8 wherein said binder comprises polyethylene.

13. The apparatus of claim 1 wherein the working electrode comprises a furnace black powder dispersed in a binder comprising a synthetic resinous thermoplastic material.

14. The apparatus of claim 13 wherein said binder comprises polyethylene.

15. The apparatus of claim 1 wherein the average particle size of the carbon black powder is between about 10 to about 100 millimicrons, and wherein the carbon black/binder matrix composition comprises about 50 percent by weight or greater of carbon black.

* * * * *

UNITED STATES PATENT AND TRADEMARK OFFICE
CERTIFICATE OF CORRECTION

PATENT NO. : 4,343,767

DATED : August 10, 1982

INVENTOR(S) : Merton W. Long et al.

It is certified that error appears in the above—identified patent and that said Letters Patent is hereby corrected as shown below:

Col. 1, line 59, delete "matrials" and insert --materials--.

Col. 2, line 49, delete "chor" and insert --chro--.

Col. 2, line 61, delete "inifinite" and insert --infinite--.

Col. 5, line 21, delete "nanometeers" and insert --nanometers--.

Col. 8, line 46, delete "60-mesh" and insert --600-mesh--.

Col. 8, line 48, delete "30°-600°C" and insert --30°-60°C--.

Col. 13, line 26, delete "Equilibrium" and insert --Equilibration--.

Col. 14, line 30, delete "these" and insert --those--.

Col. 14, line 63, delete "120" and insert --1.20--.

Col. 15, line 6, insert a comma --,-- after the word "Essentially".

UNITED STATES PATENT AND TRADEMARK OFFICE
CERTIFICATE OF CORRECTION

PATENT NO. : 4,343,767

DATED : August 10, 1982

INVENTOR(S) : Merton W. Long et al.

It is certified that error appears in the above—identified patent and that said Letters Patent is hereby corrected as shown below:

Col. 17, line 11, delete "time" and insert --times--.

Col. 18, Claim 11, line 54, delete "10", second instance, and insert --100--.

Signed and Sealed this

Twenty-third Day of November 1982

[SEAL]

Attest:

GERALD J. MOSSINGHOFF

Attesting Officer

Commissioner of Patents and Trademarks